United States Patent [19]

Plank et al.

[11] 4,128,504

[45] Dec. 5, 1978

[54] STABILIZED ZINC-CONTAINING ZEOLITES

[75] Inventors: Charles J. Plank, Woodbury; Edward J. Rosinski, Pedricktown; Edwin N. Givens, Pitman, all of N.J.

[73] Assignee: Mobil Oil Corporation, New York, N.Y.

[21] Appl. No.: 551,949

[22] Filed: Feb. 21, 1975

Related U.S. Application Data

[63] Continuation-in-part of Ser. No. 329,800, Feb. 5, 1973, abandoned.

[51] Int. Cl.$^2$ .............................................. B01J 29/06
[52] U.S. Cl. ................................................ 252/455 Z
[58] Field of Search ................................... 252/455 Z

[56] References Cited

U.S. PATENT DOCUMENTS

| | | | |
|---|---|---|---|
| 3,700,585 | 10/1972 | Chen et al. | 252/455 Z |
| 3,702,886 | 11/1972 | Argauer et al. | 252/455 Z |

*Primary Examiner*—Carl Dees
*Attorney, Agent, or Firm*—Charles A. Huggett; Raymond W. Barclay; Claude E. Setliff

[57] ABSTRACT

Crystalline aluminosilicate catalysts, especially those containing zinc, are stabilized with respect to elution of the zinc by adding thereto another metal of Group IB or Group VIII (e.g. copper or nickel). Germanium, rhenium and the rare earth metals may also be added.

24 Claims, No Drawings

STABILIZED ZINC-CONTAINING ZEOLITES

CROSS-REFERENCE TO RELATED APPLICATIONS

This application is a continuation-in-part of copending U.S. application Ser. No. 329,800, filed Feb. 5, 1973, and now abandoned.

BACKGROUND OF THE INVENTION

1. Field of the Invention

This invention relates to an improved catalyst useful in a process of preparing aromatic compounds by contacting a feed consisting essentially of $C_2$–$C_{10}$ paraffins or olefins with a crystalline aluminosilicate zeolite having a $SiO_2/Al_2O_3$ ratio of at least about 12 and a constraint index of from 1 to about 12. In particular, the invention is concerned with such zinc-containing zeolites to which another metal has been added to prevent elution of the zinc at high temperatures.

2. Discussion of the Prior Art

It is known to contact various hydrocarbon fractions with acidic catalysts such as solid siliceous acidic catalysts, including crystalline aluminosilicate zeolites. These catalysts have been used in a wide variety of reactions including cracking, isomerization, aromatization and the like. Representative United States patents concerning contacting various hydrocarbon fractions with zeolites are U.S. Pat. Nos. 3,140,249, 3,140,251, 3,140,253 and 3,140,322.

The formation of aromatic compounds from low molecular weight hydrocarbons, including paraffins, olefins and mixtures thereof, is known in the art, as taught, for example in U.S. Pat. Nos. 3,296,324 and 3,374,281.

It is also known, for example from U.S. Pat. No. 3,331,767, that in certain reactions involving 5A° pore size zeolites (erionite for example) such as hydrocracking, one of the disclosed forms of the zeolite is the zinc-containing zeolite that has been combined with another metal such as platinum, nickel or cobalt.

U.S. Pat. No. 3,700,585 teaches that the original cation of a zeolite may be replaced with, for example, zinc or with a hydrogenation component such as nickel. However, the reference does not suggest a zeolite containing in both of these. The disclosure of U.S. Pat. No. 3,702,886 is similar, but neither does it disclose a zeolite containing zinc and another metal.

SUMMARY OF THE INVENTION

In accordance with the invention there is provided a method of preventing the elution of zinc from a zinc-containing zeolite by incorporating therein an elution preventing amount of another metal selected from the group consisting of the metals of Group IB and VIII of the Periodic Table, germanium, rhenium, and the rare earths, e.g. cerium, the zeolite used having a $SiO_2/Al_2O_3$ ratio of at least about 12 and a constraint index, as hereinafter defined, of from about 1 to about 12. Examples of metals in IB and VIII are copper, gold, silver, platinum and nickel.

DESCRIPTION OF SPECIFIC EMBODIMENTS

Zinc-containing zeolites, having a $SiO_2/Al_2O_3$ ratio as hereinabove defined, especially ZSM-5 and ZSM-11, are the preferred catalysts for aromatizing paraffinic and olefinic charge stocks. The use of zinc, however, poses a problem because of its tendency to elute from the zeolite at high temperatures (e.g. about 1100° F.) in a hydrogen atmosphere. Since the Zn-containing catalyst produces large amounts of hydrogen during reaction, the hydrogen atmosphere is unavoidable. The consequent loss of zinc results in a decrease of catalyst stability. It has been discovered that the addition of certain additional metals will stop or significantly retard the elution of zinc while allowing the catalyst to maintain a high level of aromatization. While we do not wish to be bound by any theory, it would appear that these metals alloy with the Zn on the catalysts so as to reduce its vapor pressure. Thus, any metal which so alloys with the Zn should be effective for the disclosed purpose. The ones which we have found to be effective are those listed previously.

The method of this invention has a practical economic potential since the zinc-containing catalysts to which additional metals have been added are surprisingly stable under the reaction conditions employed, so they will remain active over long periods of time thereby decreasing the need for frequent regeneration.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type.

Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 4.5 |
| ZSM-35 | 4.5 |
| TMA Offretite | 3.7 |
| Beta | 0.6 |
| ZSM-4 | 0.5 |
| H-Zeolon | 0.5 |
| REY | 0.4 |

-continued

| CAS | C.I. |
|---|---|
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-21, ZSM-35, ZSM-38 and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060 (Mobil Docket 8713), filed Nov. 29, 1974. This zeolite can be identified, in terms of mole ratios of oxides and in the anhydrous state, as follows:
(0.3–2.5)R$_2$O : (0–0.8)M$_2$O : Al$_2$O$_3$ : > 8 SiO$_2$
wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:
(0.4–2.5)R$_2$O : (0–0.6)M$_2$O : Al$_2$O$_3$ : xSiO$_2$
wherein R is an organic nitrogen-containing cation derived from a 2-(hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set fort in Table I. It is observed that this X-ray diffraction pattern (significant lines) is similar to that of natural ferrierite with a notable exception being that natural ferrierite patterns exhibit a significant line at 11.33Å.

TABLE I

| d(Å) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-21 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged from. The characteristic sorption ratio n-hexane/2-methylpentane for ZSM-21 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO$_2$ | 0.05–0.5 | 0.07–0.49 |
| H$_2$O/OH⁻ | 41–500 | 100–250 |
| SiO$_2$/Al$_2$O$_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 105° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. Application Ser. No. 528,061 (Mobil Docket 8714), filed Nov. 29, 1974. This zeolite can be identified, in terms of mole ratios of oxides and in the anhydrous state, as follows:

(0.3–2.5)R$_2$O : (0–0.8)M$_2$O : Al$_2$O$_3$ : > 8 SiO$_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

(0.4–2.5)R$_2$O : (0.6) M$_2$O : Al$_2$O$_3$ : xSiO$_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33Å. Close examination of some individual samples of ZSM-35 may show a very weak line at 11.3–11.5Å. This very weak line, however, is determined not to be a significant line for ZSM-35.

| d(Å) | I/Io |
|---|---|
| 9.6 ± 0.20 | Very Strong–Very, Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may however, be activated by heating in an inert atmosphere at 1000° F. for one hour, followed by base exchange with ammonium salts and followed by a further calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The zeolites used in the instant invention may have the original replaceable ions replaced by ions which yield an acidic zeolite upon calcination. One such ion is the ammonium ion. This ion can typically be exchanged into the above described zeolite by contacting it with an ammonium chloride.

Representative ion exchange techniques are disclosed in such patents as U.S. Pat. Nos. 3,140,249, 3,140,251 and 3,140,253. The metals may also be added by impregnation.

Following contact with the salt solution of the desired replacing cation, the zeolites may be washed with water and dried at a temperature ranging from 150° F. to about 600° F. and thereafter may be heated in air or other inert gas at temperatures ranging from about 500° F. to 1700° F. for periods of time ranging from 1 to 48 hours or more.

It is also possible to treat the zeolite with steam at elevated temperatures ranging from 800° F. to 1600° F. and preferably 1000° F. and 1500° F. if such is desired. The treatment may be accomplished in atmospheres consisting partially or entirely of steam.

A similar treatment can be accomplished at lower temperatures and elevated pressures, e.g. 350°–700° F. at 10 to about 200 atmospheres.

The zinc or the zinc and additional metal may be added to pure hydrogen or ammonium form of the zeolite catalyst, preferably by ion exchange or impregnation with a salt of the metal to be added. Effective levels of each metal may range from about 0.1% by weight to about 10.0% by weight. Preferably about 0.2% to about 7% by weight. More preferably, the zinc will be present at a concentration of from about 0.1% to about 5% and the other metal from about 0.1% to about 2% by weight. Whether calcined or ammonium zeolites are used, addition of the metal is preferably followed by calcination in air at about 1000° F.

The different metals can be added to the zeolite separately, but they are conveniently and preferably added together. That is to say, salts such as $Cu(NO_3)_2$ and $Zn(NO_3)_2$ can at the same time be placed in contact with the zeolites. In addition to the nitrate salts, as here illustrated, the halide, phosphonate or sulfate salts, among others, may be used.

One embodiment of this invention resides in the use of a porous matrix together with the zeolites previously described. The zeolites can be combined, dispersed or otherwise intimately admixed with a porous matrix in such proportions that the resulting product contains from 1% to 95% by weight, and preferably from 20 to 80% by weight, of the zeolite in the final composite.

The term "porous matrix" includes inorganic compositions with which the aluminosilicates can be combined, dispersed or otherwise intimately admixed wherein the matrix may be active or inactive. It is to be understood that the porosity of the compositions employed as a matrix can either be inherent in the particular material or it can be introduced by mechanical or chemical means. Representative matrices which can be employed include metals and alloys thereof, sintered metals and sintered glass, asbestos, silicon carbide aggregates, pumice, firebrick, diatomaceous earths, and inorganic oxides. Inorganic compositions especially those of a siliceous nature are preferred. Of these matrices, inorganic oxides such as clay, chemically treated clay, silica, silica-alumina, etc., are particularly preferred because of their superior porosity, attrition resistance, and stability.

The compositing of the aluminosilicate with an inorganic oxide can be achieved by several methods wherein the aluminosilicates are reduced to a particle size less than 40 microns, preferably less than 10 microns, and intimately admixed with an inorganic oxide while the latter is in a hydrous state such as in the form of hydrosol, hydrogel, wet gelatinous precipitate, or in a dried state, or a mixture thereof.

The inorganic oxide may also consist of raw clay or a clay material which has been treated with an acid medium to render it active. The aluminosilicate can be incorporated into the clay simply by blending the two and fashioning the mixture into desired shapes. Suitable clays include attapulgite, kaolin, sepiolite, polygarskite, kaolinite, halloysite, plastic ball clays, bentonite, montmorillonite, illite, chlorite, etc.

Other useful matrices include powders of refractory oxides, such as alumina, alpha alumina, etc., having very low internal pore volume. Preferably, these materials have substantially no inherent catalytic activity of their own.

The following examples will illustrate the practice of this invention.

EXAMPLE 1

The ammonium form of ZSM-5, used to prepare various forms of the catalysts of this invention, was made as follows:

| A. Silicate Solution | |
|---|---|
| 42.2 lbs. Q brand silicate | { 28.8 wt. % $SiO_2$ <br> 8.9 wt. % $Na_2O$ <br> 62.3 wt. % $H_2O$ |
| 52.8 lbs. water | |
| Sp. Gr. 1.151 at 73° F | |
| B. Acid Solution | |
| 1.44 lbs. $Al_2(SO_4)_3 \cdot 18H_2O$ | |
| 3.52 lbs. $H_2SO_4$ | ca 97% |
| 15.8 lbs. | NaCl |
| 72.2 lbs. | $H_2O$ |
| Sp. Gr. | 1.162 at 65° F |
| C. Tripropylamine | |
| 2.84 lbs. tripropylamine | |

Solutions A and B were mixed continuously through a nozzle, flowing solution A at 960 ml/min. and solution B at 950 ml/min. The mixture flowed into a steam heated 30 gallon autoclave. Solution C, the tetrapropyl amine, was added to the total mixture. The mixture was heated in the stirred autoclave for 25 hours at 300°–315° F. At the end of this reaction period, the amine was flashed off and the reactor contents (184 lbs. of product slurry) cooled to room temperature prior to discharing into holding vessels.

Two lbs. of the above ZSM-5 product was washed on a filter funnel. One half of this wet cake was dried at 230° F. then heated to 700° F. and held for three hours. The calcined sample was then base exchanged with 5 wt. % $NH_4Cl$ solution at 190° F. while stirring. 5 ml of solution per gram of base was used. After each one hour contact the slurry was filtered, then recontacted for a total of 5 contacts. Following the $NH_4Cl$ base exchange the $NH_4ZSM$-5 was washed free of chloride ion and dried at 230° F.

A calcined sample of this $NH_4ZSM$-5 had a residual sodium content of 0.01% by weight.

EXAMPLE 2

Here 27.5 grams of a dried $NH_4ZSM$-5 similar to the product of Example 1 was contacted for 4 hours at 180°–200° F. with a solution containing 0.5 N $ZnCl_2$ and 0.5 N $NH_4Cl$. Following this contact the product was filtered, water washed free of chloride ion, dried over night at 230° F. and then pelleted and sized to 14 to 25 mesh. The sized particles were calcined for 10 hours at 1000° F. The calcined product had a residual zinc content of about 1 wt.%.

EXAMPLE 3

This ZnHZSM-5 was prepared from a portion of the $NH_4ZSM$-5 prepared according to Example 1 after being calcined for 10 hours at 1000° F. In this case 15.0 grams of the HZSM-5 was combined with ZnO powder by first mixing for 2 minutes in a blender and then ball-milling for 3 hours. The milled powder was then pelleted and sized 14 to 25 mesh. This pelleted material was used directly in the test. On analysis the product contained 4.0 wt.% zinc.

EXAMPLE 4

A sample of CuZn ZSM-5 was prepared from a batch of $NH_4$ ZSM-5 prepared according to Example 1 as follows. A 50 g. portion of the dried $NH_4ZSM$-5 was contacted for 4 hours at 188°–193° F. with 1300 ml of 0.5 $NZnCl_2$ and 450 ml of 0.5N $NH_4Cl$, with stirring. After filtering the cake was washed free of chloride at room temperature, dried for 23 hours at 230° F., then pelleted and ground to 14 to 25 mesh particles. These particles were calcined at 2° F./minute to 1000° F. and held there for 10 hours. At this stage the catalyst contained 0.75 wt.% zinc. These catalyst particles were then evacuated for one-half hour and impregnated with 4.1 ml of a 1.9% $CuCl_2.2 H_2O$ solution. After shaking by hand for two minutes the sample was dried for 17 hours at 230° F. and calcined at 2° F./minute to 1000° F. and held at 1000° for 10 hours. The resulting catalyst contained 0.45% copper.

EXAMPLE 5

This catalyst was prepared using a portion of the $NH_4ZSM$-5 made according to Example 1. The $NH_4ZSM$-5 was calcined for 10 hours at 1000° F. first and then impregnated with a combined solution of Au $Cl_3$ and $ZnCl_2$. In this impregnation 10.84 of the HZSM-5 was evacuated for one-half hour, then contacted with 7.4 ml of a solution containing 0.032g of Au $Cl_3$ and 0.229 g $ZnCl_2$. This is sufficient Au $Cl_3$ and ZnCl$_2$ to deposit 0.3% gold and 1% zinc on the catalyst. The impregnated sample was dried for 22 hours at 230° F. then calcined at 2° F./min. to 1000° F. for 10 hours at 1000° F. Analysis of the final catalyst gave a zinc content of 0.93 weight %.

EXAMPLE 6

This catalyst was prepared by using 15.08 grams of the ammonium ZSM-5 prepared in Example 1. The NH$_4$ZSM-5 was evacuated for one half hour then impregnated with 10.23 ml of a solution containing 0.319 g ZnCl$_2$ and 0.076 g Pt (as H$_2$PtCl$_6$). After shaking the mixture for 2 minutes to insure good distribution of impregnating solution over the catalyst, the catalyst was dried for 19 hours at 230° F. and then calcined for 10 hours at 1000° F. Analysis of the final catalyst showed 0.75 wt.% zinc and 0.41 wt.% platinum.

EXAMPLE 7

Here 15.08 g. of the same ammonium ZSM-5 prepared in Example 1 was evacuated for one half hour and then impregnated with 10.23 ml of solution containing 0.453 g GeCl$_4$, 0.32 g ZnCl$_2$ and acetone. After the addition of the solution to the sample it was shaken for 2 minutes and then dried for 19 hours at 230° F. This was followed by calcination for 10 hours at 1000° F. The final product on analysis contained 0.80% zinc and a calculated germanium content of 1 wt.%.

EXAMPLE 8

This AgZnHZSM-5 was prepared employing a portion of the NH$_4$ZSM-5 produced in Example 1. The NH$_4$ZSM-5 was first pelleted and sized to 14 to 25 mesh and then was calcined for 10 hours at 1000° F. Following this it was vacuum impregnated as follows. 10.26 g of HZSM-5 (product remaining after calcination) was impregnated, after one half hour evacuation, with 6.55 ml of solution containing 0.303 g Zn(NO$_3$)$_2$.6H$_2$O and 0.247 g AgNO$_3$. The combination of particles and solution was shaken for 2 minutes to incur uniform distribution of impregnating solution. Following the impregnation the sample was air dried for 18 hours at 230° F. and calcined for 10 hours at 1000° F. On analysis the product had a zinc content of 0.61 wt.% and a silver content of 1.46 wt.%.

EXAMPLE 9

In preparing the product of this Example, 15.45 grams of the calcined ammonium ZSM-5, prepared as described under Example 1, was evacuated for one half hour, then was impregnated with 10.2 ml of a solution containing 0.321g of ZnCl$_2$ and 0.985g of NiCl$_2$.6H$_2$O. The mixture of pellets and solution was shaken for 2 minutes to insure uniform distribution of the solution. Following the impregnation, the catalyst was dried for 18 hours at 230° F. and then calcined for 10 hours at 1000° F. The product, NiZnHZSM-5 contained 0.9 wt.% zinc and 0.9 wt.% nickel.

EVALUATION OF INVENTION

The following tests were designed to evaluate the ability of an added metal to diminish elution of zinc in a steady stream of hydrogen and to compare the aromatization activity of the various specimens.

Zinc Elution Test

Eight-tenths to 1.0 gm of catalyst was placed in a furnace through which hydrogen was passed at a rate of 10 cc per minute. The catalyst was heated at 1000° F. for 24 hours. Initially water condensed in the exit tube, but evaporated during the 24 hours. Visual observation was made for any deposited metal in the exit tube. After the initial 24 hours, the catalyst temperature was increased to 1100° F. and during a period of from 1 to 3 days periodic inspections were made for condensed eluted materials.

Aromatization Test

Five-tenths gm of catalyst was placed in a dual bed reactor in which the first half (0.25 gm) of the bed was at 1100° F. and the second half at 950° F. The flow rate of a 50/50 propylene-propane feed was adjusted to the WHSV shown in the table. Samples were taken between ¼ and 1¼ hours on stream and analyzed.

The tables below contain summaries of the data obtained.

TABLE I

| Catalyst | Example | % Zn | % Other Metal | ELUTION OF ZINC Hours at 1000° F | Hours at 1100° F | |
| --- | --- | --- | --- | --- | --- | --- |
| CuZnHZSM-5 | 4 | 0.75 | 0.45 | 24 | 24 | No deposit |
| AuZnHZSM-5 | 5 | .93 | .3 | 24 | 72 | No deposit at 1000° F<br>No deposit at 1100° F after 48 hours<br>Small deposit at 72 hours |
| PtZnHZSM-5 | 6 | .75 | .41 | 24 | 72 | No deposit at 1000° F<br>Trace deposit at 1100° F after 24 hours<br>Small deposit at 1100° F after 48 hours<br>Sl. increase in deposit after 72 hours |
| GeZnHZSM-5 | 7 | .80 | 1.0 | 24 | 72 | No deposit at 1000° F<br>Trace deposit at 1100° F after 24 hours<br>No additional deposit at 1100° F after 72 hrs. |
| ZnHZSM-5 | 2 | <1 | — | 21 | 3 | Deposit at 1100° F within 3 hours |
| ZnHZSM-5 | 3 | 4 | — | 24 | 48 | Deposit at 1000° F within 24 hours<br>Heavy deposit 1100° F at 24 hours<br>Very heavy deposit 1100° F at 48 hours |
| AgZnHZSM-5 | 8 | .61 | 1.46 | 24 | 72 | No deposit at 1000° F<br>No deposit at 4 hours at 1100° F<br>Sl. deposit at 24 hrs. at 1100° F<br>Heavy deposit at 72 hrs. at 1100° F |
| NiZnHZSM-5 | 9 | 0.9 | 0.9 | 24 | 24 | No deposit |

TABLE II

| Catalyst of Example | AROMATIZATION | | | | | | |
|---|---|---|---|---|---|---|---|
| | 4 | 5 | 6 | 7 | 2 | 8 | 9 |
| Temperature, °F | 1100/950 | 1100/950 | 1100/950 | 1100/950 | 1100/950 | 1100/950 | 1100/950 |
| WHSV | 3.57 | 3.32 | 3.36 | 3.47 | 3.48 | 3.47 | 3.48 |
| Based on Recovered | | | | | | | |
| Wt. % Liquid Product | 47.1 | 52.9 | 53.4 | 44.4 | 49.9 | 52.9 | 39.7 |
| Wt. % Aromatic in Liquid | 97.9 | 98.2 | 97.7 | 96.9 | 98.1 | 98.4 | 98.7 |
| Av. Mol. Wt. Aromatics | 91.9 | 91.4 | 88.6 | 90.3 | 91.4 | 91.4 | 90.9 |
| Wt. % Olefin to Aromatics | 95.2 | 106.5 | 113.8 | 93.9 | 100.9 | 97.6 | 80.8 |
| Charge | Product Composition Wt % | | | | | | |
| $C_1$ | 4.6 | 7.0 | 5.8 | 4.2 | 5.5 | 5.7 | 10.6 |
| $C_2=$ | 3.3 | 1.6 | 0.4 | 1.4 | 2.2 | 0.8 | 2.9 |
| $C_2$  1.0* | 5.9 | 9.5 | 22.1 | 5.9 | 7.1 | 7.5 | 10.8 |
| $C_3=$  49.2* (46.2)** | 12.0 | 4.2 | 3.0 | 9.5 | 4.2 | 13.3 | 8.9 |
| $C_3$  48.6* (48.4)** | 25.5 | 23.1 | 14.2 | 32.6 | 29.4 | 16.4 | 26.4 |
| $C_4=$ | 0.5 | 0.7 | 0.5 | 0.5 | 0.3 | 1.2 | 0.2 |
| $C_4$ | 0.9 | 0.7 | 0.6 | 1.1 | 1.2 | 1.6 | 0.4 |
| $C_5=$ | 0.1 | 0.2 | 0.1 | 0.2 | — | 0.3 | 0 |
| $C_5$ | 0.1 | 0.1 | — | 0.3 | 0.1 | 0.3 | 0 |
| Parrafins in Liquid | 1.0 | 1.0 | 1.3 | 1.5 | 1.0 | 0.9 | 0.6 |
| Benzene | 13.5 | 16.6 | 19.4 | 13.9 | 15.5 | 16.7 | 12.0 |
| Toluene | 19.7 | 21.8 | 24.6 | 19.2 | 20.4 | 22.4 | 17.5 |
| Xylenes | 9.0 | 8.7 | 6.0 | 7.7 | 8.7 | 8.2 | 7.1 |
| Total $C_9$ | 1.3 | 1.5 | 0.1 | 0.5 | 1.4 | 1.1 | 0.6 |
| Indane | 0.1 | 0.2 | — | 0.1 | 0.1 | 0.1 | 0.1 |
| Total $C_{10}$ | 0.2 | 0.5 | 0.2 | 0.3 | 0.4 | 0.4 | 0.2 |
| Naphthalene | 1.0 | 1.3 | 1.0 | 0.6 | 0.9 | 1.5 | 0.8 |
| Total $C_{11}^+$ | 1.2 | 1.4 | 0.8 | 0.7 | 1.5 | 1.6 | 0.7 |
| Wt. % Recovered | 100.8 | 97.4 | 99.7 | 102.8 | 96.8 | 102.5 | 94.6 |

*Example 2 only
**All other tests

It is believed that a ZnHZSM-5 catalyst containing metals other than those previously disclosed will be, for all practical purposes, relatively ineffective in diminishing zinc elution. For example SnZnHZSM-5 (0.84% zinc, 0.70% tin) showed a small deposit at 24 hours at 1000° F., with successively increasing amounts of yellow deposit at 1100° F. after 24, 48 and 72 hours. Also CdZnHZSM-5 (1.08% zinc, 0.74% cadmium) showed considerable deposit at 1000° F. at 24 hours, with no additional deposit at 48 hours at 1100° F.

We claim:

1. A method for preventing elution of zinc from a zinc-containing zeolite catalyst by incorporating therein an elution preventing amount of another metal selected from the group consisting of metals of Group IB or VIII of the Periodic Table, germanium, rhenium and rare earth metals, the zeolite used having a silica to alumina ratio of at least about 12 and a constraint index of from about 1 to about 12.

2. The method of claim 1 wherein zinc and the other metal may be present in a range from about 0.1 percent by weight to about 10 percent by weight.

3. The method of claim 2 wherein said range is from about 0.2 to about 7 percent by weight.

4. The method of claim 2 wherein the zinc is present at a concentration of from 0.1 percent by weight to about 5 percent by weight and the other metal from about 0.1 percent to about 2 percent by weight.

5. The method of claim 1 wherein the other metal is copper.

6. The method of claim 1 wherein the other metal is silver.

7. The method of claim 1 wherein the other metal is gold.

8. The method of claim 1 wherein the other metal is platinum.

9. The method of claim 1 wherein the other metal is nickel.

10. The method of claim 1 wherein the other metal is germanium.

11. The method of claim 1 wherein the other metal is rhenium.

12. The method of claim 1 wherein the zeolite used is ZSM-5.

13. The method of claim 1 wherein the zeolite used is ZSM-11.

14. The method of claim 1 wherein the final zeolite is CuZnHZSM-5.

15. A zeolite catalyst comprising of a zeolite characterized by having a silica to alumina mole ratio of at least 12 and a constraint index of from about 1 to about 12 and containing from about 0.1% to about 5% by weight of zinc and from about 0.1% to about 2% by weight of another metal selected from a group of metals of Groups IB and VIII of the Periodic Table, germanium, rhenium and rare earth metals.

16. The catalyst of claim 15 wherein the zeolite used is ZSM-5.

17. The catalyst of claim 15 wherein the zeolite used is ZSM-11.

18. The catalyst of claim 15 wherein the final zeolite is CuZnHZSM-5.

19. The catalyst of claim 15 wherein the other metal is silver.

20. The catalyst of claim 15 wherein the other metal is gold.

21. The catalyst of claim 15 wherein the other metal is platinum.

22. The catalyst of claim 15 wherein the other metal is nickel.

23. The catalyst of claim 15 wherein the other metal is germanium.

24. The catalyst of claim 15 wherein the other metal is rhenium.

* * * * *